(12) United States Patent
Tsuboi

(10) Patent No.: US 8,623,654 B2
(45) Date of Patent: Jan. 7, 2014

(54) STABILIZING AGENT FOR CONTROL MATERIAL, CONTROL MATERIAL CONTAINING THE STABILIZING AGENT, AND MEASUREMENT KIT COMPRISING THE CONTROL MATERIAL

(75) Inventor: Isami Tsuboi, Kawagoe (JP)

(73) Assignee: BML, Inc., Tokyo (JP)

( * ) Notice: Subject to any disclaimer, the term of this patent is extended or adjusted under 35 U.S.C. 154(b) by 0 days.

(21) Appl. No.: 13/254,674

(22) PCT Filed: Mar. 4, 2010

(86) PCT No.: PCT/JP2010/053501
§ 371 (c)(1),
(2), (4) Date: Sep. 2, 2011

(87) PCT Pub. No.: WO2010/101206
PCT Pub. Date: Sep. 10, 2010

(65) Prior Publication Data
US 2012/0003743 A1 Jan. 5, 2012

(30) Foreign Application Priority Data

Mar. 5, 2009 (JP) ................................. 2009-051529

(51) Int. Cl.
*G01N 33/96* (2006.01)
*G01N 33/68* (2006.01)
*G01N 33/48* (2006.01)

(52) U.S. Cl.
USPC ........ 436/16; 436/8; 436/15; 436/63; 436/86; 436/87; 436/88; 435/26

(58) Field of Classification Search
USPC ............. 436/8, 15, 16, 18, 63, 86, 87, 88, 94, 436/95, 174, 176; 422/430; 435/2, 14, 26, 435/810; 252/408.1; 568/852
See application file for complete search history.

(56) References Cited

U.S. PATENT DOCUMENTS

| | | | |
|---|---|---|---|
| 4,663,295 A | 5/1987 | Vail et al. | |
| 4,684,615 A | 8/1987 | Hoskins | |
| 4,883,762 A | 11/1989 | Hoskins | |
| 5,147,803 A | 9/1992 | Enomoto | |
| 6,309,852 B1 * | 10/2001 | Tazoe et al. | ...... 435/26 |
| 2004/0241744 A1 | 12/2004 | Kohno et al. | |
| 2005/0136499 A1 | 6/2005 | Henckel | |
| 2008/0111272 A1 * | 5/2008 | Burgess et al. | ...... 264/165 |

FOREIGN PATENT DOCUMENTS

| | | |
|---|---|---|
| EP | 0 130 708 A1 | 1/1985 |
| JP | 60-18762 A | 1/1985 |
| JP | 2-075953 A | 3/1990 |
| JP | 10-017597 A | 1/1998 |
| JP | 2000-187033 A | 7/2000 |
| JP | 2005-181326 A | 7/2005 |
| JP | 2007-107950 A | 4/2007 |
| JP | 2008-203269 A | 9/2008 |

OTHER PUBLICATIONS

International Preliminary Report on Patentability dated Oct. 27, 2011 in International Application No. PCT/JP2010/053501.
Ken-Ichi Izutsu et al: Excipient crystallinity and its protein-structure stabilizing effect during freeze-drying; The Journal of Pharmacy and Pharmacology, vol. 54, No. 8, Aug. 1, 2002, pp. 1033-1039.
Mendez D L et al: The effect of non-enzymatic glycation on the unfolding of human serum albumin; Archives of Biochemistry and Biophysics, Academic Press, US, vol. 444, No. 2, Dec. 15, 2005; pp. 92-99.
Database Biosis [Online]; Biosciences Information Service, Philadelphia, PA, US; (1990), S. Yoshioka et al: Variations of Free Non-Glucose Polyols Content in Serum from Patients with Diabetes Mellitus and Their Correlation with Hemoglobin A-1C, 2 pages.
Extended European Search Report for Application No. 10748799.3-2404 / 2405275 PCT/JP2010053501 dated Jan. 10, 2013.
Japanese Office Action in corresponding Application No. 2010-515713 dated Aug. 13, 2013.

* cited by examiner

*Primary Examiner* — Maureen Wallenhorst
(74) *Attorney, Agent, or Firm* — Sughrue Mion, PLLC

(57) ABSTRACT

An object of the present invention is to provide a control material which can be preferably employed in detection of 1,5-anhydro-D-glucitol and glycoalbumin, which are employed as excellent indices for diabetes. The present inventor has found that mannitol which is added to serum or plasma used as control material stabilizes 1,5-anhydro-D-glucitol and glycoalbumin present in the serum or plasma for a long period of time, and that the object can be attained through provision of (1) an agent for stabilizing control material, the agent being composed of mannitol and (2) control material containing mannitol and 1,5-anhydro-D-glucitol.

8 Claims, 2 Drawing Sheets

STABILIZING AGENT FOR CONTROL MATERIAL, CONTROL MATERIAL CONTAINING THE STABILIZING AGENT, AND MEASUREMENT KIT COMPRISING THE CONTROL MATERIAL

CROSS REFERENCE TO RELATED APPLICATIONS

This application is a National Stage of International Application No. PCT/JP2010/053501 filed Mar. 4, 2010, the contents of which are incorporated herein by reference in their entirety.

TECHNICAL FIELD

The present invention relates to control material which has improved storage stability of glycoalbumin and 1,5-anhydro-D-glucitol.

BACKGROUND ART

Strict control of blood glucose levels of diabetes patients is very important to prevent onset of a complication such as retinopathy, nephropathy, or neuropathy. Hemoglobin $A_{1c}$, glycoalbumin, fructosamine, 1,5-anhydro-D-glucitol, or the like has come into practical use, as an index of determination of control status of blood glucose.

Among these indices, glycoalbumin, which reflects the control status of blood glucose for the past 1 to 2 weeks, is thought to be useful for the short-term control, in order to deal with various problems in diabetes control such as the timing of start of drug administration, pregnancy, trauma, and acute complications. 1,5-Anhydro-D-glucitol, which is a polyol present in the human body, is known to be lost when sugar urine is excreted, and concomitantly, blood 1,5-anhydro-D-glucitol level drops rapidly. Therefore, diabetes patients have a considerably low level of 1,5-anhydro-D-glucitol. As is also known, when blood glucose is poorly controlled, blood 1,5-anhydro-D-glucitol level rapidly lowers, and gradually returns to a normal level at a constant rate if good status of blood glucose is continued. Since 1,5-anhydro-D-glucitol also reflects blood glucose variation within a relatively short period and exhibits considerably large variation in a slight hyperglycemia zone, 1,5-anhydro-D-glucitol serves as a useful index for more strictly controlling blood glucose level or for assessing the effect of therapy for diabetes.

When a target component in a specimen is detected, control material whose quality is stable is preferably employed as reference material. However, when a lyophilized control material is reconstituted upon use, deterioration of the component in the control material is problematically caused. This problem is solved by adding a stabilizing agent to control material. For example, sucrose (saccharose) is added as a stabilizing agent for hemoglobin $A_{1c}$ (Patent Document 1), and a disaccharide (e.g., sucrose) is added as a stabilizing agent for glycoalbumin (Patent Document 2).

PRIOR ART DOCUMENTS

Patent Documents

Patent Document 1: Japanese Patent Application (kokai) No. Hei 10-17597
Patent Document 2: Japanese Patent Application (kokai) No. 2007-107950

SUMMARY OF THE INVENTION

Problems to be Solved by the Invention

As described above, a variety of suitable biochemical indices for controlling diabetes are currently available. Therefore, in addition to a case where a single test is performed, two or more different tests are performed in combination in some cases for establishing more suitable diabetes therapeutic strategies. Even in the case where such multiple tests are performed, calibration must be performed. Rather than performing calibration for each test item, it is more efficient and economical to reduce the number of calibrations to be performed to the possibly smallest number. Thus, an object of the present invention is to provide a control material which can be favorably employed in detection of 1,5-anhydro-D-glucitol and glycoalbumin, which are currently employed as excellent indices for diabetes.

Means for Solving the Problems

Quite surprisingly, the present inventor has found that, when mannitol is added to serum or plasma which is used as control material, the stability of 1,5-anhydro-D-glucitol and glycoalbumin present in the serum or plasma can be maintained for a long period of time, and accomplished the present invention.

Accordingly, in a first aspect of the present invention, there is provided a stabilizing agent for control serum or plasma, the agent being composed of mannitol (hereinafter may be referred to as the stabilizing agent of the present invention). In a second aspect of the present invention, there is provided a control serum or plasma containing mannitol and 1,5-anhydro-D-glucitol (hereinafter may be referred to as 1,5-AG) (hereinafter may be referred to as the control material of the present invention). In a third aspect of the present invention, there is provided an assay kit for glycoalbumin and/or 1,5-AG, the kit comprising as an element the control material of the present invention (hereinafter may be referred to as the assay kit of the present invention).

In the present invention, mannitol is predominantly D-mannitol, but either L-mannitol or DL-mannitol (racemic form) may be employed. Since L-mannitol is not a natural sugar and is not easily available, i.e., is a rare sugar, the mannitol of the invention is substantially D-mannitol. In other words, the mannitol employed in the present invention is most preferably D-mannitol.

In the present invention, the serum is a component obtained by removing hemocytes (including platelets) and fibrinogen from blood, and the plasma is a component obtained by removing hemocytes (including platelets) from blood. The serum or plasma employed in the present invention may be in the form of liquid, or solid (powder) produced through lyophilization or the like.

Effects of the Invention

According to the present invention, a stabilizing agent for a control material is provided, which can stabilize over time a control material (control serum or control plasma) which is employed in detection of 1,5-AG and/or glycoalbumin, which are currently employed as excellent indices for diabetes. The present invention also provides a control material stabilized with the stabilizing agent, and an assay kit for glycoalbumin and/or 1,5-AG, the kit comprising as an element the control material.

BRIEF DESCRIPTION OF THE DRAWINGS

FIG. 1(2) is a graph showing a change over time in relative glycoalbumin level after addition of each candidate component for a stabilizing agent, which shows results of high-level material.

FIG. 2(2) is a graph showing a long-term change over time in relative glycoalbumin level after addition of D-mannitol and sucrose, which shows results of high-level material.

MODES FOR CARRYING OUT THE INVENTION

Figure 1:
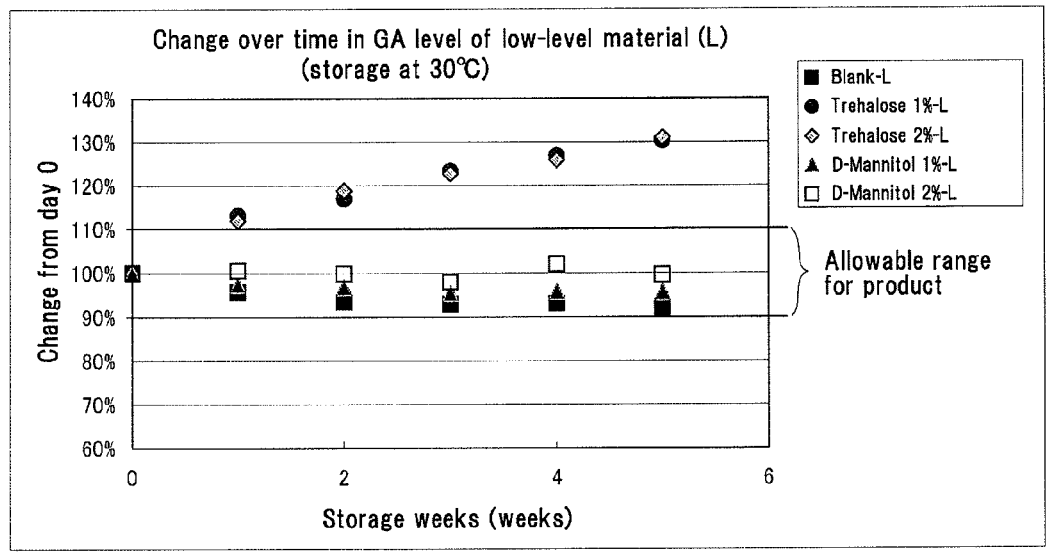
FIG. 1(1) is a graph showing a change over time in relative glycoalbumin level after addition of each candidate component for a stabilizing agent, which shows results of low-level material.
Figure 1:
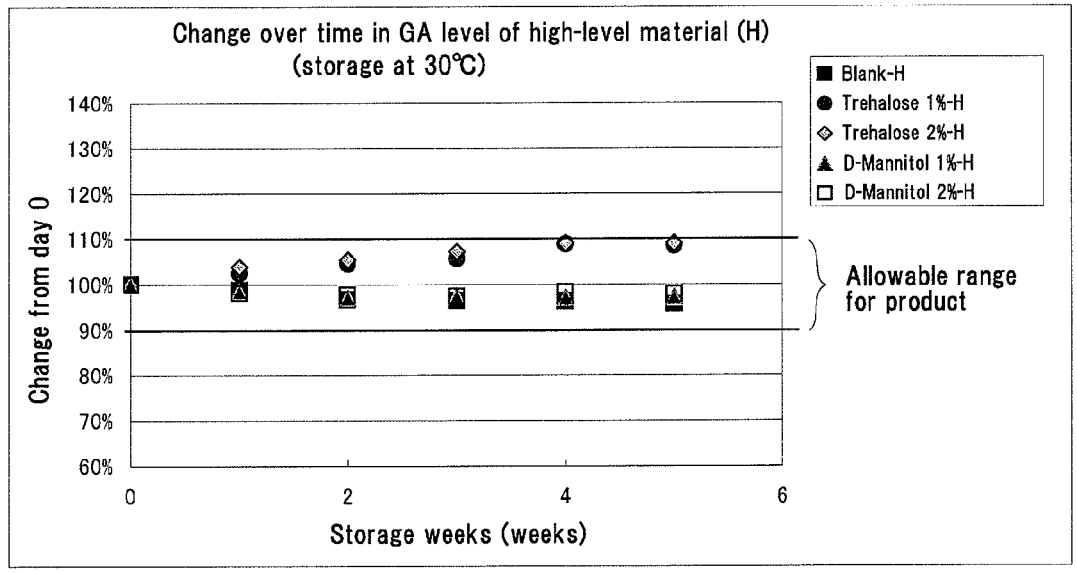

[The Stabilizing Agent of the Present Invention]
(1) Substantial Component of the Stabilizing Agent of the Present Invention The stabilizing agent of the present invention contains mannitol as a substantial component. D-mannitol (suitable component) which may be used in the present invention may be a naturally-derived or synthetic product, which may be a commercial product or a manufactured product. L-mannitol (rare sugar) which may be used in the present invention is a synthetic product, which may be a commercial product or a manufactured product.

Mannitol ($C_6H_{14}O_6$) is a sugar alcohol of mannose. D-mannitol is present in a wide range of plants and is known to be a predominant component of manna from *Fraxinus ornus* L., etc. D-Mannitol is also known to be rich in brown algae. For example, D-mannitol can be readily obtained by subjecting cut pieces of kelp or kombu to extraction with hot ethanol. Alternatively, D-mannitol may be produced by electrically or catalytically reducing D-glucose or invert sugar under alkaline conditions, followed by epimerization and reduction. Still alternatively, D-mannitol may be produced through fermentation of glucose, sucrose, etc. with a mold belonging to the genus *Aspergillus*. L-mannitol is known to be produced through, for example, reduction of L-mannose with sodium amalgam or reduction of L-mannosacchanolactone under a pressure of 80 atmospheres in the presence of a platinum catalyst.

The stabilizing agent of the present invention may be composed of mannitol. However, it may contain, if necessary, additives such as a vehicle, another stabilizing agent, etc., within the range of types and amounts so as not to impede stabilization of glycoalbumin and 1,5-AG contained in serum or plasma which is to be stabilized (hereinafter may be referred to as serum or the like).

In one embodiment of the invention, the stabilizing agent is added to serum or the like to which 1,5-AG has been optionally added, and the thus-obtained mixture as is, or a solidified (powdered) product thereof (obtained through lyophilization or a similar technique) may be used. In general, 1,5-AG intrinsically present in serum or the like is removed, and then a predetermined amount of a new aliquot of 1,5-AG is added thereto, in order to adjust the 1,5-AG content to fall within a specific range and provide uniform product quality. Also in the present invention, the step of removing 1,5-AG intrinsically present in serum or the like is preferably performed in the preparation of the control material of the present invention. However, alternatively, no 1,5-AG removing step may be performed. Regardless of performance of the step of removing 1,5-AG intrinsically present in serum or the like, when the control material of the present invention has a low 1,5-AG level (low-level material), the 1,5-AG content of serum or the like preferably falls within the range of 4 to 6 µg/mL, and, when the control material of or the like preferably falls within the range of 4 to 6 µg/mL, and, when the control material of the present invention has a high 1,5-AG level (high-level material), it preferably falls within the range of 13 to 17 µg/mL.

The amount of the stabilizing agent of the present invention added to serum or the like is, as reduced to the mass of mannitol, preferably 1 to 20 mass/vol. %, more preferably 2 to 10 mass/vol. %, most preferably 2 to 3 mass/vol. %. When the amount of mannitol added to the serum or the like is less than 1 mass/vol. %, difficulty is encountered in sufficiently stabilizing glycoalbumin and 1,5-AG, whereas when the amount is in excess of 20 mass/vol. %, enhancement in stabilization of glycoalbumin and 1,5-AG commensurate with the addition is difficult.

As described above, the stabilizing agent of the present invention is used for stabilizing a control serum or the like which is preferably employed in calibration performed in determination of glycoalbumin and/or 1,5-AG.

(2) Determination of Glycoalbumin

Determination of glycoalbumin by use of a control serum or the like which has been stabilized by the stabilizing agent of the present invention may be performed with reference to, for example, the disclosure in Patent Document 2. Specifically, it exemplifies an enzymatic method in which (1) glycoalbumin present in a serum sample or the like is digested by a protease such as pronase or proteinase K, to thereby form fructosylammino acid; (2) ketoaminoxidase or fructosamine oxidase is caused to act on the thus-formed fructosylammino acid serving as a substrate in the presence of oxygen, to thereby generate hydrogen peroxide; and (3) the hydrogen peroxide is quantitated (e.g., color is developed by causing peroxidase to act on hydrogen peroxide in the presence of, for example, 4-aminoantipyrine and N-ethyl-N-(2-hydroxy-3-sulfopropyl)-m-toluidine, and then absorbance determination at 550 nm is performed to determine the quantity of hydrogen peroxide).

The above determination may be performed by use of a commercial agent, Lucica GA-L series (product of Asahi Kasei Pharma Corporation).

In the determination of glycoalbumin, preferably, the total albumin of a serum sample or the like whose glycoalbumin level is to be determined is determined separately.

No particular limitation is imposed on the method of determining total albumin, and examples of the method include immuno-nephelometry, the latex method, and the dye method.

The glycoalbumin level of the serum sample or the like can be correctly determined (detected) by correction through dividing the aforementioned glycoalbumin level by the total albumin level.

One most preferred embodiment of the detection process includes (a) a step of determining the glycoalbumin level of a serum sample or the like, by using, as a reference material, a control material containing natural albumin; (b) a step of determining the total albumin level of the serum sample or the like; and (c) a step of correction through dividing measurement (a) by measurement (b), wherein the three steps are performed automatically.

Those skilled in the art can readily perform the steps automatically by means of a known automatic assay apparatus for serum samples or the like with appropriate tuning depending on the detection mode.

(3) Determination of 1,5-AG

Determination of 1,5-AG by use of a control serum or the like which has been stabilized by the stabilizing agent of the present invention is also preferably performed through the enzymatic method. Currently, two procedures are generally known as an enzymatic method for determining 1,5-AG.

A first procedure includes the following sequential steps (1) to (3):

(1) causing ADP-dependent hexokinase and adenosine 5'-diphosphate to come in contact with 1,5-AG present in a specimen, to thereby form 1,5-AG 6-phosphate;

(2) causing 1,5-AG dehydrogenase to act on the thus-formed 1,5-AG 6-phosphate and oxidized β-nicotinamide adenine dinucleotide phosphate, to thereby form reduced β-nicotinamide adenine dinucleotide phosphate (NADPH); and (3) detecting the thus-formed reduced β-nicotinamide adenine dinucleotide phosphate, to thereby quantitate 1,5-AG.

In the first procedure, 1,5-AG may be determined by means of a commercial kit, Determiner L 1,5-AG (product of Kyowa Medex Co., Ltd.). In the commercial kit, NADPH (in (3) above) is detected by causing diaphorase to act on NADPH and a tetrazolium salt (2-(4-iodophenyl)-3-(4-nitrophenyl)-5-(2,4-disulfophenyl)-2H-tetrazolium sodium salt), to thereby produce a water-soluble formazan dye, followed by colorimetric analysis.

In a second procedure, pyranose oxidase is employed as an oxidase for 1,5-AG, and the hydroxyl group at the 2-position of 1,5-AG is oxidized to generate hydrogen peroxide. The thus-generated hydrogen peroxide is detected by use of peroxidase through a colorimetric method. In the second procedure, since pyranose oxidase also reacts with glucose, glucose must be made unreactive in advance to pyranose oxidase.

In the second procedure, 1,5-AG is determined by use of a commercial kit, Lana (registered trademark) 1,5 AG Auto liquid (product of Nippon Kayaku Co., Ltd.). In the commercial kit, glucose is made unreactive via phosphorylation in the presence of glucokinase.

In the present invention, either the first procedure or the second procedure may be carried out for determining 1,5-AG. However, through employment of the first procedure, the advantages of the present invention can be more effectively attained.

[The Control Material of the Present Invention]

As described above, the control material of the present invention is a control serum or a control plasma which contains mannitol and 1,5-AG. As used herein, the expression "containing 1,5-AG" is used in referring to serum or the like containing 1,5-AG which is intrinsically contained in the serum or the like or which is externally added thereto. Preferably, the control material of the present invention has a 1,5-AG content of 4 to 6 μg/mL with respect to the serum or the like in the case where the control material is a low-1,5-AG-level material, and it has a 1,5-AG content of 13 to 17 μg/mL with respect to the serum or the like in the case where it is a high-1,5-AG-level material. The 1,5-AG which is intentionally and externally added thereto may be produced through a method generally known in the art or may be a commercial product. The compound 1,5-AG may be produced by reducing the 1-position of α-D-glucose or by causing a reductase to act on 1,5-anhydrofructose.

As described above, the amount of mannitol added to serum or the like is preferably 1 to 20 mass/vol. % as reduced to the mass of mannitol, with respect to the serum or the like, more preferably 2 to 10 mass/vol. %, most preferably 2 to 3 mass/vol. %.

For the purpose of, for example, preventing denaturation of glycoalbumin, the control material of the present invention may further contain, in addition to the aforementioned essential ingredients, an optional ingredient, so long as the desired effect of the present invention is not impaired. Examples of the optional ingredient added into the control material of the present invention include ascorbic acid, a salt of triphosphoric acid, catechin, sodium sulfite, sodium hydrogensulfite, ferrous sulfate, and glutathione.

As has been known, when serum or the like is used as control material, the serum is generally subjected to a preliminary treatment such as removal of miscellaneous matters. The control material of the present invention is also allowed to be subjected to a treatment which is generally performed to serum or the like. Examples of the treatment include dialysis, filtration, centrifugation (removal of chylomicron and insoluble matter), and concentration.

In order to fully attain the long-term stabilization effect, the control material of the present invention is most preferably a lyophilized product. The lyophilized product may be prepared through a method generally known in the art. For example, a sample is frozen at −30° C. to −40° C. and placed under reduced pressure. Then, it is stored at −20° C. to 4° C. for about 5 to about 100 hours for drying, to thereby yield a lyophilized preparation of interest. In particular, in order to completely dry mannitol present in the control material of the present invention, the drying is preferably performed for about 90 to about 100 hours.

[The Assay Kit of the Present Invention]

As described above, the assay kit of the present invention for glycoalbumin and/or 1,5-AG contains, as an element, the control material of the present invention as a reference material. In addition to the aforementioned control material of the present invention serving as a reference material for detection, if required, the assay kit of the present invention may further contain, as optional kit elements, (1) an element for determining glycoalbumin, such as non-glycoalbumin, an assay reagent for determining the quantity of glycoalbumin through an enzymatic method, etc., and (2) an element for determining 1,5-AG, such as an assay reagent for determining the quantity of 1,5-AG through an enzymatic method.

In the case where the assay kit of the present invention contains, as an element for determining 1,5-AG, an assay reagent for performing the aforementioned first 1,5-AG determination procedure, the assay kit may include ADP-dependent hexokinase, diaphorase, ADP, NADPH$^+$, 2-(4-iodophenyl)-3-(4-nitrophenyl)-5-(2,4-disulfophenyl)-2H-tetrazolium sodium salt, 1,5-AG 6-phosphate dehydrogenase, etc., if required. In the case where the assay kit of the present invention contains an assay reagent for performing the aforementioned second 1,5-AG determination procedure, the assay kit may include a preliminary treatment liquid such as 4-aminoantipyrine, and a coloring liquid such as pyranose oxidase, peroxidase, N-ethyl-N-(2-hydroxy-3-sulfopropyl)-3-methylaniline sodium dehydrate, etc., if required.

In addition to an element(s) required for determining glycoalbumin and/or 1,5-AG, the assay kit of the present invention may contain an element required for other assay items, if required. Examples of such assay items include blood albumin level, total protein level, glucose level, etc.

EXAMPLES

The present invention will next be described in detail by way of examples, which should not be construed as limiting the invention thereto. Unless otherwise specified, the sucrose content, D mannitol content, or the like of serum or the like has a unit of (%), specifically, the percentage of mass of a component to volume of the serum or the like.

Referential Example

Treatment of a Pool Serum

The pool serum employed in Test Example 1 described hereinbelow was prepared by subjecting an untreated serum obtained by thawing a frozen serum of a healthy subject in a refrigerator, to dialysis, concentration, centrifugation, and filtration. In dialysis, the untreated serum charged into a dialysis tube was immersed in cold physiological saline, and dialysis was performed in a cold and dark place. Subsequently, concentration was performed by use of polyethylene glycol. In centrifugation, the thus-concentrated serum was centrifuged at 4° C. for about 20 minutes at a rotational rate of 10,000 rpm, and the supernatant was recovered. Finally, the thus-obtained serum which had been subjected to centrifugation was filtered under pressure, whereby a treated serum of interest was yielded.

Test Example 1

Studies on Storage Stability of 1,5-AG

To physiological saline and the treated serum samples prepared in Referential Example, sucrose or D-mannitol was added at a concentration of 0 to 10%. Immediately after addition, the 1,5-AG level of each sample was determined, in an automated analyzer Hitachi 7170 maintained at 37° C., by means of a commercial assay kit based on the aforementioned first procedure, Determiner L 1,5-AG (product of Kyowa Medex Co., Ltd.), and by means of a commercial assay kit based on the aforementioned second procedure, Lana (registered trademark) 1,5 AG Auto liquid (product of Nippon Kayaku Co., Ltd.). The results are shown in Tables 1-1 to 1-4 below. The sequential steps of Test Example 1 were carried out at ambient temperature (about 20 to about 30° C.). Hereinafter, the assay system according to the first procedure is referred to as a "first assay system," and the assay system according to the second procedure is referred to as a "second assay system." The measurements given in the Tables have a unit of μg/mL. The aforementioned treated serum had been provided in an amount sufficient for performing the Test Example.

TABLE 1-1

(Sugar) Sucrose/physiological saline

| Sugar level (W/V %) | First assay system | Second assay system |
|---|---|---|
| 0% | 0.5 | 0.0 |
| 1% | 1.0 | 0.0 |
| 5% | 3.2 | −0.1 |
| 10% | 6.0 | 0.0 |

TABLE 1-2

(Sugar) Sucrose/treated serum

| Sugar level (W/V %) | First assay system | Second assay system |
|---|---|---|
| 0% | 0.6 | −0.1 |
| 1% | 1.2 | 0.0 |

TABLE 1-2-continued (Sugar) Sucrose/treated serum

| Sugar level (W/V %) | First assay system | Second assay system |
|---|---|---|
| 5% | 3.4 | 0.2 |
| 10% | 6.3 | 0.5 |

TABLE 1-3

(Sugar) D-Mannitol/physiological saline

| Sugar level (W/V %) | First assay system | Second assay system |
|---|---|---|
| 0% | 0.5 | 0.0 |
| 1% | 0.5 | 0.0 |
| 5% | 0.6 | 0.0 |
| 10% | 0.6 | 0.0 |

TABLE 1-4

(Sugar) D-Mannitol/treated serum

| Sugar level (W/V %) | First assay system | Second assay system |
|---|---|---|
| 0% | 0.6 | −0.1 |
| 1% | 0.7 | 0.0 |
| 5% | 0.7 | 0.0 |
| 10% | 0.8 | 0.0 |

As is clear from Tables 1-1 to 1-4, in the second assay systems employing sucrose, no substantial non-specific reaction was observed. However, a reaction corresponding to a non-specific reaction was observed in the first assay systems employing sucrose. In contrast, no substantial reaction corresponding to a non-specific reaction was observed in the first and second assay systems employing D-mannitol. Thus, D-mannitol was found to have an excellent effect of stabilizing 1,5-AG in a control material.

Test Example 2

Studies on Candidate Stabilizing Agent for a Multi Control Material for Glycoalbumin and 1,5-AG Test Example 1 has revealed that D-mannitol stabilizes 1,5-AG in serum. Test Example 2 was carried out so as to find a stabilizing agent suitable for a "multi control material for glycoalbumin and 1,5-AG." As candidate stabilizing agents, D-mannitol and trehalose were tested. Specifically, low-level material and high-level material were prepared, and a candidate stabilizing agent was added to each material at a concentration of 1% or 2%. In each test system, the mixture was put into ninety of 10-mL-capacity vials (3 g/vial), and the contents of the vials were lyophilized. Then, the vials were closely sealed with a stopper and stored at 30° C. Over the course of five weeks, one vial was selected every one week, and the contents of the vial were dissolved in purified water (3 mL), and glycoalbumin (GA), albumin (ALB), total protein (TP), 1,5-AG, and GA % were determined. In the assay, glycoalbumin, albumin, and GA % were determined by means of Lucica GA-L ALB (product of Asahi Kasei Pharma Corporation), total protein (TP) was determined by means of Total Protein II-HA Test Wako (product of Wako Pure Chemical Industries, Ltd.), and 1,5-AG was determined by means of the aforementioned "Determiner L 1,5-AG." The low-level material and high-level material had been provided in amounts sufficient for performing Test Example 2.

Preparation of Low-Level Material

Low-level material was prepared by adding 1,5-AG to the "treated serum" prepared in Referential Example so as to adjust the 1,5-AG concentration to 5.4 µg/4 mL.

Preparation of High-Level Material

Before preparation of high-level material, artificially glucose-elevated serum was prepared. Specifically, an untreated serum obtained by thawing a frozen serum of a healthy subject in a refrigerator was used, as in Referential Example. Then, glucose was added to and dissolved in the serum to attain a glucose concentration of 5 mass %, and the mixture was centrifuged in a manner similar to that of Referential Example. The thus-centrifuged serum was filtered under pressure and sterilized via filtration. The thus-filter-sterilized serum was incubated at 37° C. for two days under sterilized conditions. The incubated serum was immersed in cold physiological saline, and dialysis was performed in a cold and dark place. Subsequently, concentration was performed by use of polyethylene glycol. Furthermore, the thus-concentrated serum was centrifuged in a manner similar to that as described above, and then subjected to suction filtration, and the serum which had been subjected to suction filtrate was employed as artificially glucose-elevated serum of interest.

High-level material was prepared by mixing the aforementioned "treated serum" and "artificially glucose-elevated serum" so that GA was adjusted to about 1.6 g/dL, ALB to about 5 g/dL, TP to about 8 g/dL, and GA % to about 40%. GA, ALB, TP, and GA % were determined by means of the aforementioned commercial kits in a similar manner. Subsequently, 1,5-AG was added to the mixed serum so as to adjust the 1,5-AG concentration to 16.3 µg/mL, to obtain a high-level material of interest. Tables 2-1 to 2-10 show the results.

TABLE 2-1

| Storage period (wks) | Blank (low-level material) | | | | |
|---|---|---|---|---|---|
| | GA | ALB | TP | 1,5-AG | GA % |
| 0 | 0.584 | 4.48 | 7.58 | 5.7 | 14.3 |
| 1 | 0.559 | 4.42 | 7.62 | 5.8 | 14.0 |
| 2 | 0.546 | 4.39 | 7.57 | 6.0 | 13.8 |
| 3 | 0.542 | 4.35 | 7.46 | 6.0 | 13.8 |
| 4 | 0.543 | 4.47 | 7.55 | 6.1 | 13.6 |
| 5 | 0.535 | 4.46 | 7.56 | 5.9 | 13.4 |
| Detection unit | g/dL | g/dL | g/dL | µg/mL | % |

TABLE 2-2

| Storage period (wks) | Blank (high-level material) | | | | |
|---|---|---|---|---|---|
| | GA | ALB | TP | 1,5-AG | GA % |
| 0 | 1.705 | 4.40 | 7.58 | 16.1 | 36.9 |
| 1 | 1.685 | 4.36 | 7.62 | 16.2 | 36.8 |
| 2 | 1.649 | 4.40 | 7.65 | 16.6 | 35.8 |
| 3 | 1.645 | 4.37 | 7.54 | 16.7 | 35.9 |
| 4 | 1.642 | 4.43 | 7.54 | 16.8 | 35.4 |
| 5 | 1.630 | 4.43 | 7.61 | 16.7 | 35.2 |
| Detection unit | g/dL | g/dL | g/dL | µg/mL | % |

TABLE 2-3

| Storage period (wks) | Trehalose 1% added (low-level material) | | | | |
|---|---|---|---|---|---|
| | GA | ALB | TP | 1,5-AG | GA % |
| 0 | 0.577 | 4.42 | 7.55 | 5.8 | 14.3 |
| 1 | 0.653 | 4.34 | 7.58 | 5.9 | 16.1 |
| 2 | 0.675 | 4.39 | 7.62 | 6.2 | 16.4 |

TABLE 2-3-continued

| Storage period (wks) | Trehalose 1% added (low-level material) | | | | |
|---|---|---|---|---|---|
| | GA | ALB | TP | 1,5-AG | GA % |
| 3 | 0.712 | 4.38 | 7.54 | 6.2 | 17.1 |
| 4 | 0.732 | 4.43 | 7.56 | 6.0 | 17.4 |
| 5 | 0.752 | 4.39 | 7.56 | 6.0 | 17.9 |
| Detection unit | g/dL | g/dL | g/dL | µg/mL | % |

TABLE 2-4

| Storage period (wks) | Trehalose 1% added (high-level material) | | | | |
|---|---|---|---|---|---|
| | GA | ALB | TP | 1,5-AG | GA % |
| 0 | 1.727 | 4.36 | 7.60 | 16.5 | 36.9 |
| 1 | 1.771 | 4.36 | 7.59 | 16.2 | 38.6 |
| 2 | 1.806 | 4.38 | 7.66 | 16.8 | 39.2 |
| 3 | 1.826 | 4.42 | 7.53 | 16.6 | 39.4 |
| 4 | 1.881 | 4.46 | 7.60 | 16.8 | 40.3 |
| 5 | 1.873 | 4.46 | 7.61 | 16.6 | 39.7 |
| Detection unit | g/dL | g/dL | g/dL | µg/mL | % |

TABLE 2-5

| Storage period (wks) | Trehalose 2% added (low-level material) | | | | |
|---|---|---|---|---|---|
| | GA | ALB | TP | 1,5-AG | GA % |
| 0 | 0.576 | 4.40 | 7.56 | 5.8 | 14.4 |
| 1 | 0.645 | 4.30 | 7.55 | 5.9 | 16.1 |
| 2 | 0.685 | 4.39 | 7.64 | 6.2 | 16.6 |
| 3 | 0.707 | 4.32 | 7.46 | 6.1 | 17.2 |
| 4 | 0.725 | 4.38 | 7.56 | 6.0 | 17.4 |
| 5 | 0.755 | 4.41 | 7.59 | 5.9 | 17.9 |
| Detection unit | g/dL | g/dL | g/dL | µg/mL | % |

TABLE 2-6

| Storage period (wks) | Trehalose 2% added (high-level material) | | | | |
|---|---|---|---|---|---|
| | GA | ALB | TP | 1,5-AG | GA % |
| 0 | 1.709 | 4.39 | 7.56 | 16.2 | 37.1 |
| 1 | 1.776 | 4.28 | 7.57 | 16.2 | 39.3 |
| 2 | 1.803 | 4.36 | 7.58 | 16.6 | 39.2 |
| 3 | 1.834 | 4.30 | 7.49 | 16.6 | 40.3 |
| 4 | 1.865 | 4.39 | 7.55 | 16.6 | 40.2 |
| 5 | 1.865 | 4.35 | 7.56 | 16.6 | 40.5 |
| Detection unit | g/dL | g/dL | g/dL | µg/mL | % |

TABLE 2-7

| Storage period (wks) | D-Mannitol 1% added (low-level material) | | | | |
|---|---|---|---|---|---|
| | GA | ALB | TP | 1,5-AG | GA % |
| 0 | 0.571 | 4.40 | 7.62 | 5.6 | 14.3 |
| 1 | 0.555 | 4.35 | 7.57 | 5.7 | 14.1 |
| 2 | 0.553 | 4.37 | 7.61 | 5.9 | 14.0 |
| 3 | 0.545 | 4.31 | 7.56 | 5.8 | 14.0 |
| 4 | 0.547 | 4.40 | 7.60 | 5.9 | 13.8 |
| 5 | 0.546 | 4.36 | 7.57 | 5.7 | 13.9 |
| Detection unit | g/dL | g/dL | g/dL | µg/mL | % |

TABLE 2-8

| | D-Mannitol 1% added (high-level material) | | | | |
|---|---|---|---|---|---|
| Storage period (wks) | GA | ALB | TP | 1,5-AG | GA % |
| 0 | 1.709 | 4.35 | 7.59 | 16.0 | 37.3 |
| 1 | 1.684 | 4.36 | 7.59 | 16.5 | 36.8 |
| 2 | 1.662 | 4.37 | 7.64 | 16.5 | 36.3 |
| 3 | 1.666 | 4.32 | 7.52 | 16.5 | 36.7 |
| 4 | 1.661 | 4.38 | 7.58 | 16.0 | 36.2 |
| 5 | 1.664 | 4.36 | 7.58 | 16.4 | 36.4 |
| Detection unit | g/dL | g/dL | g/dL | µg/mL | % |

TABLE 2-9

| | D-Mannitol 2% added (low-level material) | | | | |
|---|---|---|---|---|---|
| Storage period (wks) | GA | ALB | TP | 1,5-AG | GA % |
| 0 | 0.567 | 4.35 | 7.48 | 5.6 | 14.3 |
| 1 | 0.571 | 4.27 | 7.44 | 5.8 | 14.6 |
| 2 | 0.566 | 4.31 | 7.52 | 6.0 | 14.4 |
| 3 | 0.555 | 4.29 | 7.45 | 5.7 | 14.2 |
| 4 | 0.578 | 4.35 | 7.48 | 6.1 | 14.6 |
| 5 | 0.565 | 4.34 | 7.49 | 5.8 | 14.3 |
| Detection unit | g/dL | g/dL | g/dL | µg/mL | % |

TABLE 2-10

| | D-Mannitol 2% added (high-level material) | | | | |
|---|---|---|---|---|---|
| Storage period (wks) | GA | ALB | TP | 1,5-AG | GA % |
| 0 | 1.713 | 4.38 | 7.61 | 16.1 | 37.2 |
| 1 | 1.680 | 4.33 | 7.58 | 16.2 | 37.0 |
| 2 | 1.673 | 4.32 | 7.61 | 16.3 | 36.9 |
| 3 | 1.669 | 4.29 | 7.49 | 16.2 | 37.0 |
| 4 | 1.684 | 4.34 | 7.57 | 16.4 | 36.9 |
| 5 | 1.676 | 4.34 | 7.54 | 16.2 | 36.6 |
| Detection unit | g/dL | g/dL | g/dL | µg/mL | % |

FIG. 1(1) is a graph showing changes over time of relative GA levels of low-level material, and FIG. 1(2) is a graph showing changes over time of relative GA levels of high-level material, when the measurements of GA levels on day 0 is 100%. In the graphs, the vertical axis represents the relative GA levels (median: 100%), and the horizontal axis represents the weeks of storage. The allowable range of GA variation from day 0 for the product is 100±10%.

As is clear from the graphs, low-level material to which trehalose had been added exhibited variations in glycoalbumin (GA) level falling outside the allowable range, but low-level material to which D-mannitol had been added exhibited variations in GA level falling within the allowable range. High-level material to which trehalose had been added also exhibited variations in GA level falling outside the allowable range, but high-level material to which D-mannitol had been added exhibited variations in GA level falling within the allowable range. The material to which D-mannitol had been added exhibited no variation in albumin level or TP level.

These results have revealed that addition of D-mannitol caused no variation in 1,5-AG level and simultaneously caused no variation in glycoalbumin level, and therefore, D-mannitol was a remarkably excellent stabilizing agent for the multi control material.

Test Example 3

Comparison of Mannitol with Sucrose as a Stabilizing Agent

In Test Example 3, the utility of mannitol which is used as the stabilizing agent of the present invention was compared with that of sucrose through a long-term storage test.

Specifically, in a manner similar to that of Test Example 2, low-level material and high-level material were prepared, and D-mannitol (2%) was added to each material and sucrose (10%) was added to each material. In each test system, the mixture was put into 30 of 10-mL-capacity vials (3 g/vial), and the contents of the vials were lyophilized. Then, the vials were closely sealed with a stopper and stored in a refrigerator maintained at 10° C. for 13 months. Five vials were selected at each of month 0 (immediately after lyophilization), month 1, month 6, month 12, and month 13, and the contents of the vials were dissolved in purified water (3 mL). In a manner similar to that of Test Example 2, glycoalbumin (GA), albumin (ALB), total protein (TP), and 1,5-AG were determined (duplicate assay). The stability of each component was evaluated as "with long-term stability," when the variation in relative measurements with respect to the initial (month 0) measurement fell within a range of ±8% throughout the test period. The low-level material and high-level material had been provided in amounts sufficient for performing Test Example 3.

Figure 2:
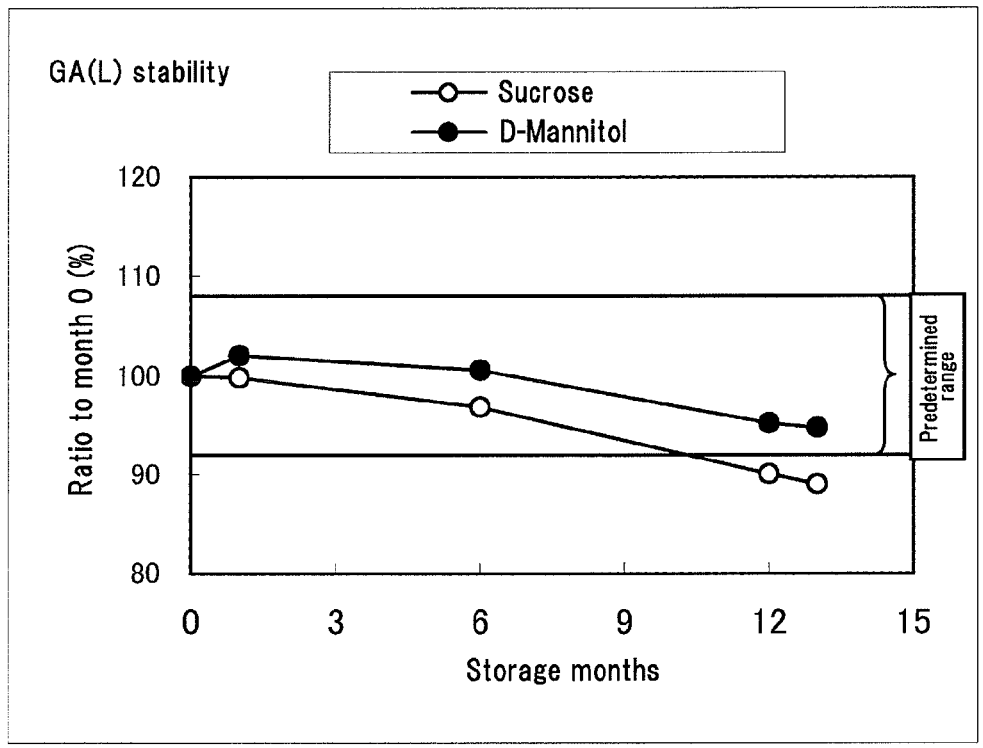
FIG. 2(1) is a graph showing a long-term change over time in relative glycoalbumin level after addition of D-mannitol and sucrose, which shows results of low-level material.
Figure 2:
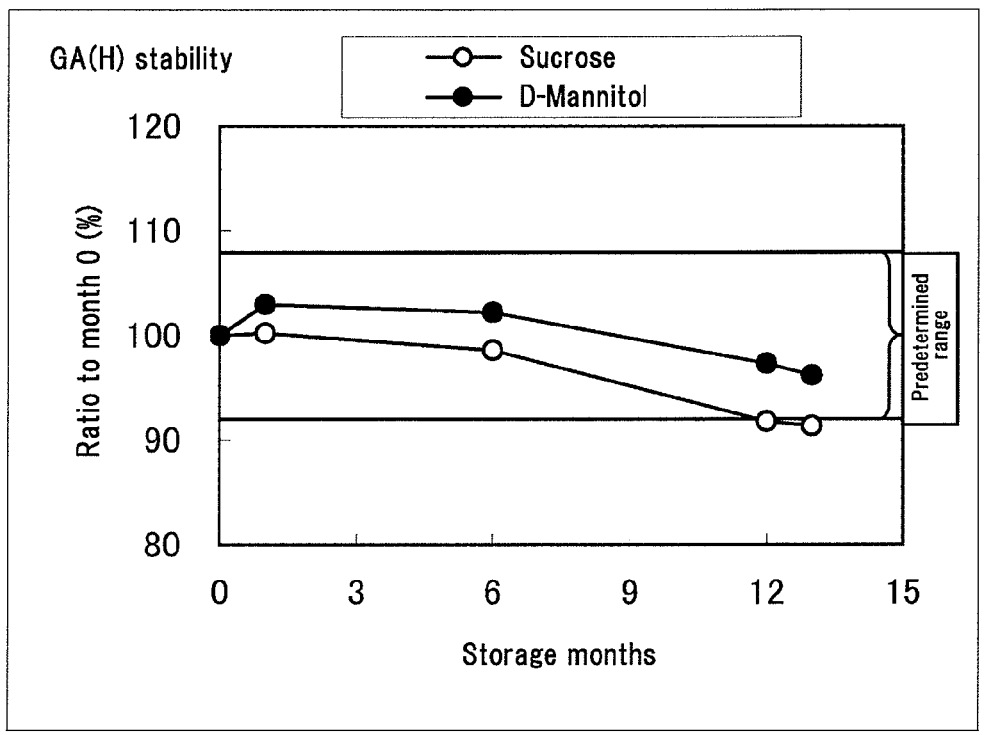

Test Example 3 has revealed that "long-term stability" was found with respect to ALB, TP, and 1,5-AG by D-mannitol and sucrose. However, a difference in stability of GA was found between the cases of D-mannitol and sucrose. Table 3 (Table 3-1: averaged measurement, Table 3-2: ratio (%) of averaged measurement with respect to month 0 measurement) shows the results. FIGS. 2(1) and 2(2) show the changes over time of GA level in Test Example 3. In the graphs, the vertical axis represents the relative GA levels (with respect to month 0 measurement), and the horizontal axis represents the storage test period (months). In the graphs, a predetermined range of GA variation of ±8% is specified.

TABLE 3-1

| | Sucrose | | D-Mannitol | |
|---|---|---|---|---|
| | L | H | L | H |
| GA (g/dL) | | | | |
| 0 month | 0.580 | 1.584 | 0.537 | 1.686 |
| 1 month | 0.579 | 1.586 | 0.548 | 1.736 |
| 6 months | 0.561 | 1.560 | 0.540 | 1.723 |
| 12 months | 0.522 | 1.453 | 0.511 | 1.640 |
| 13 months | 0.516 | 1.446 | 0.509 | 1.621 |
| ALB (g/dL) | | | | |
| 0 month | 4.68 | 4.67 | 4.30 | 4.69 |
| 1 month | 4.69 | 4.68 | 4.32 | 4.72 |
| 6 months | 4.68 | 4.69 | 4.31 | 4.73 |
| 12 months | 4.51 | 4.50 | 4.14 | 4.54 |
| 13 months | 4.49 | 4.44 | 4.10 | 4.49 |
| TP (g/dL) | | | | |
| 0 month | 7.58 | 7.60 | 7.01 | 7.59 |
| 1 month | 7.62 | 7.62 | 7.09 | 7.70 |
| 6 months | 7.66 | 7.63 | 7.06 | 7.66 |
| 12 months | 7.40 | 7.39 | 6.82 | 7.38 |
| 13 months | 7.27 | 7.26 | 6.72 | 7.25 |
| 1,5-AG (µg/mL) | | | | |
| 0 month | 5.7 | 15.8 | 5.4 | 14.7 |
| 1 month | 5.8 | 16.0 | 5.5 | 14.9 |

TABLE 3-1-continued

|  | Sucrose | | D-Mannitol | |
|---|---|---|---|---|
|  | L | H | L | H |
| 6 months | 5.9 | 16.1 | 5.5 | 15.0 |
| 12 months | 5.8 | 16.0 | 5.4 | 14.8 |
| 13 months [Ref.] | 5.8 | 16.0 | 5.5 | 14.8 |
| GLU (mg/dL) | | | | |
| 0 month | — | — | — | — |
| 1 month | −0.2 | −0.2 | −0.6 | 0.0 |
| 6 months | 0.0 | 0.0 | 0.0 | 1.0 |
| 12 months | 0.0 | 0.0 | 0.0 | 0.6 |
| 13 months | 0.0 | 0.0 | 0.2 | 1.0 |

TABLE 3-2

|  | Sucrose | | D-Mannitol | |
|---|---|---|---|---|
|  | L | H | L | H |
| GA | | | | |
| 0 month | 100.0 | 100.0 | 100.0 | 100.0 |
| 1 month | 99.8 | 100.2 | 102.0 | 103.0 |
| 6 months | 96.8 | 98.5 | 100.5 | 102.1 |
| 12 months | 90.0 | 91.7 | 95.2 | 97.3 |
| 13 months | 89.0 | 91.3 | 94.7 | 96.1 |
| ALB | | | | |
| 0 month | 100.0 | 100.0 | 100.0 | 100.0 |
| 1 month | 100.3 | 100.1 | 100.4 | 100.6 |
| 6 months | 100.0 | 100.5 | 100.0 | 100.9 |
| 12 months | 96.4 | 96.3 | 96.2 | 96.8 |
| 13 months | 95.9 | 95.1 | 95.2 | 95.8 |
| TP | | | | |
| 0 month | 100.0 | 100.0 | 100.0 | 100.0 |
| 1 month | 100.5 | 100.4 | 101.2 | 101.4 |
| 6 months | 101.0 | 100.5 | 100.8 | 100.9 |
| 12 months | 97.5 | 97.2 | 97.3 | 97.2 |
| 13 months | 96.0 | 95.6 | 95.8 | 95.5 |
| 1,5-AG | | | | |
| 0 month | 100.0 | 100.0 | 100.0 | 100.0 |
| 1 month | 103.2 | 101.1 | 102.4 | 100.9 |
| 6 months | 104.4 | 101.6 | 102.8 | 101.9 |
| 12 months | 102.7 | 101.1 | 100.7 | 100.4 |
| 13 months | 101.8 | 101.2 | 102.1 | 100.4 |

As is clear from Table 3, the test system employing D-mannitol exhibited excellent long-term GA storage stability despite a small amount (2%) of addition, as compared with the test system employing sucrose in a large amount (10%).

The invention claimed is:

1. A method for performing calibration of an assay for determining glycoalbumin in serum or plasma comprising performing the assay with control serum or control plasma containing D-mannitol and glycoalbumin as a lyophilized control material.

2. The method according to claim 1, wherein the control serum or control plasma has a D-mannitol content of 1 to 20 mass/vol. % as measured before lyophilization.

3. The method according to claim 1, wherein the control serum or control plasma has a D-mannitol content of 1 to 10 mass/vol. % as measured before lyophilization.

4. The method according to claim 1, wherein the control serum or control plasma has a D-mannitol content of 2 to 10 mass/vol. % as measured before lyophilization.

5. The method according to claim 1, wherein the control serum or control plasma has a D-mannitol content of 1 to 3 mass/vol. % as measured before lyophilization.

6. The method according to claim 1, wherein the control serum or control plasma has a D-mannitol content of 2 to 3 mass/vol. % as measured before lyophilization.

7. The method according to claim 1, wherein glycoalbumin is determined along with 1,5-anhydro-D-glucitol in the assay, and the control serum or control plasma further contains 1,5-anhydro-D-glucitol.

8. The method according to claim 7, wherein 1,5-anhydro-D-glucitol is determined in the assay through the following sequential steps (1) to (3):
   (1) causing ADP-dependent hexokinase and adenosine 5′-diphosphate to come in contact with 1,5-anhydro-D-glucitol present in a specimen, to thereby form 1,5-anhydro-D-glucitol 6-phosphate;
   (2) causing 1,5-anhydro-D-glucitol dehydrogenase to act on the 1,5-anhydro-D-glucitol 6-phosphate and oxidized β-nicotinamide adenine dinucleotide phosphate, to thereby form reduced β-nicotinamide adenine dinucleotide phosphate; and
   (3) detecting the reduced β-nicotinamide adenine dinucleotide phosphate, to thereby quantitate 1,5-anhydro-D-glucitol.

* * * * *